(12) United States Patent
Tassoni et al.

(10) Patent No.: US 11,154,412 B2
(45) Date of Patent: Oct. 26, 2021

(54) MEDICAL DEVICE RELEASE SYSTEM

(71) Applicant: BOSTON SCIENTIFIC SCIMED, INC., Maple Grove, MN (US)

(72) Inventors: Nicholas Lee Tassoni, Andover, MN (US); Eric Dinges, Edina, MN (US); Kevin McConnell, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 174 days.

(21) Appl. No.: 16/264,864

(22) Filed: Feb. 1, 2019

(65) Prior Publication Data

US 2019/0231566 A1 Aug. 1, 2019

Related U.S. Application Data

(60) Provisional application No. 62/625,054, filed on Feb. 1, 2018.

(51) Int. Cl.
*A61F 2/95* (2013.01)
*A61F 2/24* (2006.01)
(Continued)

(52) U.S. Cl.
CPC .......... *A61F 2/95* (2013.01); *A61B 17/00234* (2013.01); *A61B 17/12022* (2013.01);
(Continued)

(58) Field of Classification Search
CPC .... A61F 2/24; A61F 2/95; A61F 2/958; A61F 2/966; A61F 2/07; A61F 2/954;
(Continued)

(56) References Cited

U.S. PATENT DOCUMENTS 3,342,179 A * 9/1967 Ellmann ............... A61M 5/158
604/408
5,117,839 A 6/1992 Dance
(Continued)

FOREIGN PATENT DOCUMENTS

EP 2777542 A2 9/2014
EP 2777545 A2 9/2014
(Continued)

OTHER PUBLICATIONS

International Search Report and Written Opinion dated Apr. 5, 2019 for International Application No. PCT/US2019/016245.
(Continued)

*Primary Examiner* — Vi X Nguyen
(74) *Attorney, Agent, or Firm* — Seager, Tufte & Wickhem LLP

(57) ABSTRACT

A medical device system may include an elongate shaft having a lumen extending from a proximal end to a distal end, a release wire disposed within the lumen of the elongate shaft configured to releasably attach a medical device to the distal end of the elongate shaft, and a securement member fixedly attached to the proximal end of the elongate shaft and to a proximal end of the release wire. A proximal portion of the securement member may be configured to translate proximally away from the proximal end of the elongate shaft upon application of a proximally-directed force to the proximal portion of the securement member while the elongate shaft is maintained in a fixed position, wherein the proximal portion remains connected to the proximal end of the elongate shaft after proximal translation away from the proximal end of the elongate shaft.

10 Claims, 9 Drawing Sheets

(51) Int. Cl.
*A61B 17/00* (2006.01)
*A61B 17/12* (2006.01)
*A61M 25/00* (2006.01)
*A61F 2/966* (2013.01)
*A61F 2/01* (2006.01)

(52) U.S. Cl.
CPC ...... *A61F 2/2439* (2013.01); *A61B 17/12109* (2013.01); *A61B 2017/00292* (2013.01); *A61B 2017/00862* (2013.01); *A61B 2017/12054* (2013.01); *A61F 2/011* (2020.05); *A61F 2/9517* (2020.05); *A61F 2002/9505* (2013.01); *A61F 2002/9511* (2013.01); *A61F 2002/9534* (2013.01); *A61F 2002/9665* (2013.01); *A61M 2025/0042* (2013.01)

(58) Field of Classification Search
CPC . A61F 2/2439; A61B 17/00; A61B 17/00234; A61B 2017/12054; A61B 17/12022; A61B 17/12109; A61B 2017/12022; A61B 2017/00292
See application file for complete search history.

(56) References Cited

U.S. PATENT DOCUMENTS

| | | |
|---|---|---|
| 5,234,437 A | 8/1993 | Sepetka |
| 5,250,071 A | 10/1993 | Palermo |
| 5,282,478 A | 2/1994 | Fleischhaker, Jr. et al. |
| 5,304,195 A | 4/1994 | Twyford, Jr. et al. |
| 5,312,415 A | 5/1994 | Palermo |
| 5,546,958 A | 8/1996 | Thorud et al. |
| 5,925,059 A | 7/1999 | Palermo et al. |
| RE37,117 E | 3/2001 | Palermo |
| 6,277,125 B1 | 8/2001 | Barry et al. |
| 6,491,646 B1 | 12/2002 | Blackledge |
| 7,044,134 B2 | 5/2006 | Khairkhahan et al. |
| 7,708,755 B2 | 5/2010 | Davis et al. |
| 7,815,661 B2 | 10/2010 | Mirizzi et al. |
| 7,896,899 B2 | 3/2011 | Patterson et al. |
| 8,142,456 B2 | 3/2012 | Rosqueta |
| 8,236,042 B2 | 8/2012 | Berez et al. |
| 8,333,786 B2 | 12/2012 | Mirizzi et al. |
| 8,333,796 B2 | 12/2012 | Tompkins et al. |
| 8,641,777 B2 | 2/2014 | Strauss et al. |
| 8,696,701 B2 | 4/2014 | Becking et al. |
| 8,747,597 B2 | 6/2014 | Rosqueta et al. |
| 8,795,313 B2 | 8/2014 | Liang et al. |
| 8,801,746 B1 | 8/2014 | Kreidler et al. |
| 8,911,487 B2 | 12/2014 | Bennett et al. |
| 9,017,350 B2 | 4/2015 | Karabey et al. |
| 9,017,361 B2 | 4/2015 | Karabey et al. |
| 9,060,773 B2 | 6/2015 | Nguyen et al. |
| 9,119,948 B2 | 9/2015 | Lee et al. |
| 9,186,151 B2 | 11/2015 | Tompkins et al. |
| 9,198,670 B2 | 12/2015 | Hewitt et al. |
| 9,301,827 B2 | 4/2016 | Strauss et al. |
| 9,307,999 B2 | 4/2016 | Li et al. |
| 9,468,442 B2 | 10/2016 | Huynh et al. |
| 9,498,226 B2 | 11/2016 | Cage et al. |
| 9,549,740 B2 | 1/2017 | Rees |
| 9,554,805 B2 | 1/2017 | Tompkins et al. |
| 9,700,322 B2 | 7/2017 | Dias et al. |
| 2006/0036281 A1 | 2/2006 | Patterson et al. |
| 2006/0212055 A1 | 9/2006 | Karabey et al. |
| 2006/0229669 A1 | 10/2006 | Mirizzi et al. |
| 2006/0282159 A1 | 12/2006 | Taheri |
| 2007/0135826 A1 | 6/2007 | Zaver et al. |
| 2007/0186933 A1 | 8/2007 | Domingo et al. |
| 2007/0270903 A1 | 11/2007 | Davis et al. |
| 2007/0282373 A1 | 12/2007 | Ashby et al. |
| 2007/0293928 A1 | 12/2007 | Tomlin |
| 2008/0109059 A1 | 5/2008 | Gordon et al. |
| 2008/0119891 A1 | 5/2008 | Miles et al. |
| 2008/0300616 A1 | 12/2008 | Que et al. |
| 2009/0043331 A1 | 2/2009 | Buiser et al. |
| 2009/0062838 A1 | 3/2009 | Brumleve et al. |
| 2009/0062845 A1 | 3/2009 | Tekulve |
| 2009/0163934 A1 | 6/2009 | Raschdorf, Jr. et al. |
| 2009/0177261 A1 | 7/2009 | Teoh et al. |
| 2009/0270978 A1 | 10/2009 | Virkler et al. |
| 2009/0287291 A1 | 11/2009 | Becking et al. |
| 2009/0287294 A1 | 11/2009 | Rosqueta et al. |
| 2010/0106178 A1 | 4/2010 | Obermiller et al. |
| 2010/0121350 A1 | 5/2010 | Mirigian |
| 2010/0174269 A1 | 7/2010 | Tompkins et al. |
| 2011/0166588 A1 | 7/2011 | Connor et al. |
| 2011/0184454 A1 | 7/2011 | Barry et al. |
| 2011/0202085 A1 | 8/2011 | Loganathan et al. |
| 2011/0238147 A1 | 9/2011 | Bennett et al. |
| 2011/0265943 A1 | 11/2011 | Rosqueta et al. |
| 2011/0319926 A1 | 12/2011 | Becking et al. |
| 2012/0041470 A1 | 2/2012 | Shrivastava et al. |
| 2012/0046687 A1 | 2/2012 | Trommeter et al. |
| 2012/0197299 A1 | 8/2012 | Fabian, Jr. |
| 2012/0203322 A1 | 8/2012 | Eells |
| 2012/0283812 A1 | 11/2012 | Lagodzki |
| 2012/0316598 A1 | 12/2012 | Becking et al. |
| 2012/0330341 A1 | 12/2012 | Becking et al. |
| 2012/0330347 A1 | 12/2012 | Becking et al. |
| 2012/0330348 A1 | 12/2012 | Strauss et al. |
| 2013/0066360 A1 | 3/2013 | Becking et al. |
| 2013/0072961 A1 | 3/2013 | Cage et al. |
| 2013/0085520 A1 | 4/2013 | Liang et al. |
| 2013/0085522 A1 | 4/2013 | Becking et al. |
| 2013/0152941 A1 | 6/2013 | Nguyen et al. |
| 2013/0253572 A1 | 9/2013 | Molaei et al. |
| 2013/0261730 A1 | 10/2013 | Bose et al. |
| 2013/0296917 A1 | 11/2013 | Rees |
| 2013/0331882 A1 | 12/2013 | Tompkins et al. |
| 2014/0058434 A1 | 2/2014 | Jones et al. |
| 2014/0058435 A1 | 2/2014 | Jones et al. |
| 2014/0128907 A1 | 5/2014 | Hui et al. |
| 2014/0135810 A1 | 5/2014 | Divino et al. |
| 2014/0135811 A1 | 5/2014 | Divino et al. |
| 2014/0135812 A1 | 5/2014 | Divino et al. |
| 2014/0148843 A1 | 5/2014 | Strauss et al. |
| 2014/0172001 A1 | 6/2014 | Becking et al. |
| 2014/0236127 A1 | 8/2014 | Lee et al. |
| 2014/0358175 A1 | 12/2014 | Tompkins et al. |
| 2015/0005807 A1 | 1/2015 | Lagodzki et al. |
| 2015/0073524 A1 | 3/2015 | Bennett et al. |
| 2015/0112378 A1 | 4/2015 | Torp |
| 2015/0157332 A1 | 6/2015 | Obermiller et al. |
| 2015/0196304 A1 | 7/2015 | Rabkin et al. |
| 2015/0230802 A1 | 8/2015 | Lagodzki et al. |
| 2015/0257763 A1 | 9/2015 | Blum et al. |
| 2015/0272589 A1 | 10/2015 | Lorenzo |
| 2015/0297240 A1 | 10/2015 | Divino et al. |
| 2015/0327868 A1 | 11/2015 | Islak et al. |
| 2015/0335333 A1 | 11/2015 | Jones et al. |
| 2015/0342611 A1 | 12/2015 | Leopold et al. |
| 2015/0343181 A1 | 12/2015 | Bradway et al. |
| 2016/0008003 A1 | 1/2016 | Kleshinski et al. |
| 2016/0022445 A1 | 1/2016 | Ruvalcaba et al. |
| 2016/0030052 A1 | 2/2016 | Cragg et al. |
| 2016/0166257 A1 | 6/2016 | Allen et al. |
| 2016/0192942 A1 | 7/2016 | Strauss et al. |
| 2016/0228123 A1 | 8/2016 | Anderson et al. |
| 2016/0228124 A1 | 8/2016 | Trommeter et al. |
| 2016/0228128 A1 | 8/2016 | Connolly |
| 2016/0317274 A1 | 11/2016 | Liu et al. |
| 2017/0224350 A1 | 8/2017 | Shimizu et al. |

FOREIGN PATENT DOCUMENTS

| | | |
|---|---|---|
| EP | 3085310 A1 | 10/2016 |
| JP | 2016537134 A | 12/2016 |
| WO | 0232496 A1 | 4/2002 |
| WO | 2007047111 A1 | 4/2007 |
| WO | 2007070797 A2 | 6/2007 |
| WO | 2010030993 A1 | 3/2010 |
| WO | 2010098804 A1 | 9/2010 |

(56) References Cited

FOREIGN PATENT DOCUMENTS

| WO | 2014145012 A2 | 9/2014 |
| WO | 2014145005 A3 | 4/2015 |
| WO | 2017192394 A1 | 11/2017 |

OTHER PUBLICATIONS

International Search Report & Written Opinion dated Jun. 15, 2018 for International Application No. PCT/US2018/021978.
PCT Application No. PCT/US2017/061779 International Search Report and Written Opinion, dated Feb. 26, 2018.
International Search Report and Written Opinion dated Jul. 13, 2018 for International Application No. PCT/US2018/028240.
International Search Report and Written Opinion dated Dec. 5, 2018 for International Application No. PCT/US2018/000148.

* cited by examiner

MEDICAL DEVICE RELEASE SYSTEM

CROSS-REFERENCE TO RELATED APPLICATIONS

This application claims the benefit of priority under 35 U.S.C. § 119 to U.S. Provisional Application Ser. No. 62/625,054, filed Feb. 1, 2018, the entirety of which is incorporated herein by reference.

TECHNICAL FIELD

The present disclosure pertains to medical devices and methods for manufacturing and/or using medical devices. More particularly, the present disclosure pertains to configurations of a system for releasing medical implants.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first aspect, a medical device system may comprise an elongate shaft having a lumen extending from a proximal end of the elongate shaft to a distal end of the elongate shaft; a release wire disposed within the lumen of the elongate shaft, wherein the release wire is configured to releasably attach a medical device to the distal end of the elongate shaft; and a securement member fixedly attached to the proximal end of the elongate shaft and to a proximal end of the release wire. A proximal portion of the securement member may be configured to translate proximally away from the proximal end of the elongate shaft upon application of a proximally-directed force to the proximal portion of the securement member while the elongate shaft is maintained in a fixed position. The proximal portion remains connected to the proximal end of the elongate shaft after proximal translation away from the proximal end of the elongate shaft.

In addition or alternatively, and in a second aspect, the proximal portion of the securement member is fixedly attached to the proximal end of the release wire and a distal portion of the securement member is fixedly attached to the proximal end of the elongate shaft.

In addition or alternatively, and in a third aspect, the distal portion of the securement member is a coil spring.

In addition or alternatively, and in a fourth aspect, the coil spring is configured to bias the proximal portion of the securement member distally toward the proximal end of the elongate shaft.

In addition or alternatively, and in a fifth aspect, the coil spring undergoes elastic deformation during proximal translation of the proximal portion of the securement member up to a predetermined axial location.

In addition or alternatively, and in a sixth aspect, upon releasing the proximal portion of the securement member after proximal translation of the proximal portion of the securement member up to the predetermined axial location, the coil spring translates the proximal portion of the securement member distally toward the proximal end of the elongate shaft.

In addition or alternatively, and in a seventh aspect, the coil spring undergoes plastic deformation after proximal translation of the proximal portion of the securement member axially past the predetermined axial location.

In addition or alternatively, and in an eighth aspect, upon releasing the proximal portion of the securement member after proximal translation of the proximal portion of the securement member axially past the predetermined axial location, an axial position of the proximal portion of the securement member remains substantially fixed relative to the proximal end of the elongate shaft.

In addition or alternatively, and in a ninth aspect, proximal translation of the proximal portion of the securement member away from the proximal end of the elongate shaft translates the release wire axially relative to the elongate shaft.

In addition or alternatively, and in a tenth aspect, the proximal portion of the securement member is visually distinguishable from the elongate shaft.

In addition or alternatively, and in an eleventh aspect, a medical device system may comprise an elongate shaft having a lumen extending from a proximal end of the elongate shaft to a distal end of the elongate shaft; a medical device disposed proximate the distal end of the elongate shaft; a release wire disposed within the lumen of the elongate shaft, wherein the release wire releasably secures the medical device to the distal end of the elongate shaft; a securement member fixedly attached to the proximal end of the elongate shaft and to a proximal end of the release wire; and a microcatheter configured to deliver the medical device to a treatment site, the elongate shaft and the medical device being slidably disposed within a lumen of the microcatheter. A proximal portion of the securement member may be configured to translate proximally away from the proximal end of the elongate shaft upon application of a proximally-directed force to the proximal portion of the securement member while the elongate shaft is maintained in a fixed position. The proximal portion remains connected to the proximal end of the elongate shaft after proximal translation away from the proximal end of the elongate shaft.

In addition or alternatively, and in a twelfth aspect, the distal portion of the securement member is disposed proximal of the microcatheter when the medical device is disposed distal of the microcatheter.

In addition or alternatively, and in a thirteenth aspect, the proximal portion of the securement member assumes a non-linear configuration when unconstrained.

In addition or alternatively, and in a fourteenth aspect, the elongate shaft includes a first portion of a release mechanism attached to the distal end of the elongate shaft and the medical device includes a second portion of the release mechanism attached to a proximal end of the medical device;

wherein the release wire interlocks the first portion of the release mechanism with the second portion of the release mechanism when the proximal portion of the securement member is biased distally by the distal portion of the securement member.

In addition or alternatively, and in a fifteenth aspect, the medical device system may further comprise an introducer configured to load the medical device into the microcatheter. Proximal withdrawal of the introducer over the securement member positions the proximal portion of the securement member into a substantially linear configuration while the proximal portion is disposed within the introducer.

In addition or alternatively, and in a sixteenth aspect, a method of delivering a medical device to a treatment site may comprise:

inserting a microcatheter into a patient's anatomy and guiding a distal end of the microcatheter to a location adjacent the treatment site;

inserting a medical device disposed at a distal end of an elongate shaft into a proximal end of a lumen disposed within the microcatheter;

wherein the medical device is releasably attached to the distal end of the elongate shaft by a pull wire extending through a lumen within the elongate shaft, and wherein a securement member extends proximally from the elongate shaft, the securement member being fixedly attached to the elongate shaft and the pull wire;

advancing the medical device through the microcatheter to the treatment site; translating a proximal portion of the securement member proximally away from a proximal end of the elongate shaft while the elongate shaft is maintained in a fixed position to translate the pull wire relative to the elongate shaft, thereby releasing the medical device from the elongate shaft;

wherein the proximal portion of the securement member remains connected to the proximal end of the elongate shaft after proximal translation away from the proximal end of the elongate shaft.

In addition or alternatively, and in a seventeenth aspect, the proximal portion of the securement member is fixedly attached to the pull wire and a distal portion of the securement member is fixedly attached to the elongate shaft.

In addition or alternatively, and in an eighteenth aspect, a first portion of a release mechanism is attached to the distal end of the elongate shaft and a second portion of the release mechanism is attached to a proximal end of the medical device.

In addition or alternatively, and in a nineteenth aspect, the pull wire is slidably disposed within the distal portion of the securement member, the elongate shaft, the first portion of the release mechanism, and the second portion of the release mechanism.

In addition or alternatively, and in a twentieth aspect, upon releasing the proximal portion of the securement member after proximal translation of the proximal portion of the securement member up to the predetermined axial location, the proximal portion of the securement member is biased toward the proximal end of the elongate shaft. Upon releasing the proximal portion of the securement member after proximal translation of the proximal portion of the securement member axially past the predetermined axial location, an axial position of the proximal portion of the securement member remains substantially fixed relative to the proximal end of the elongate shaft.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
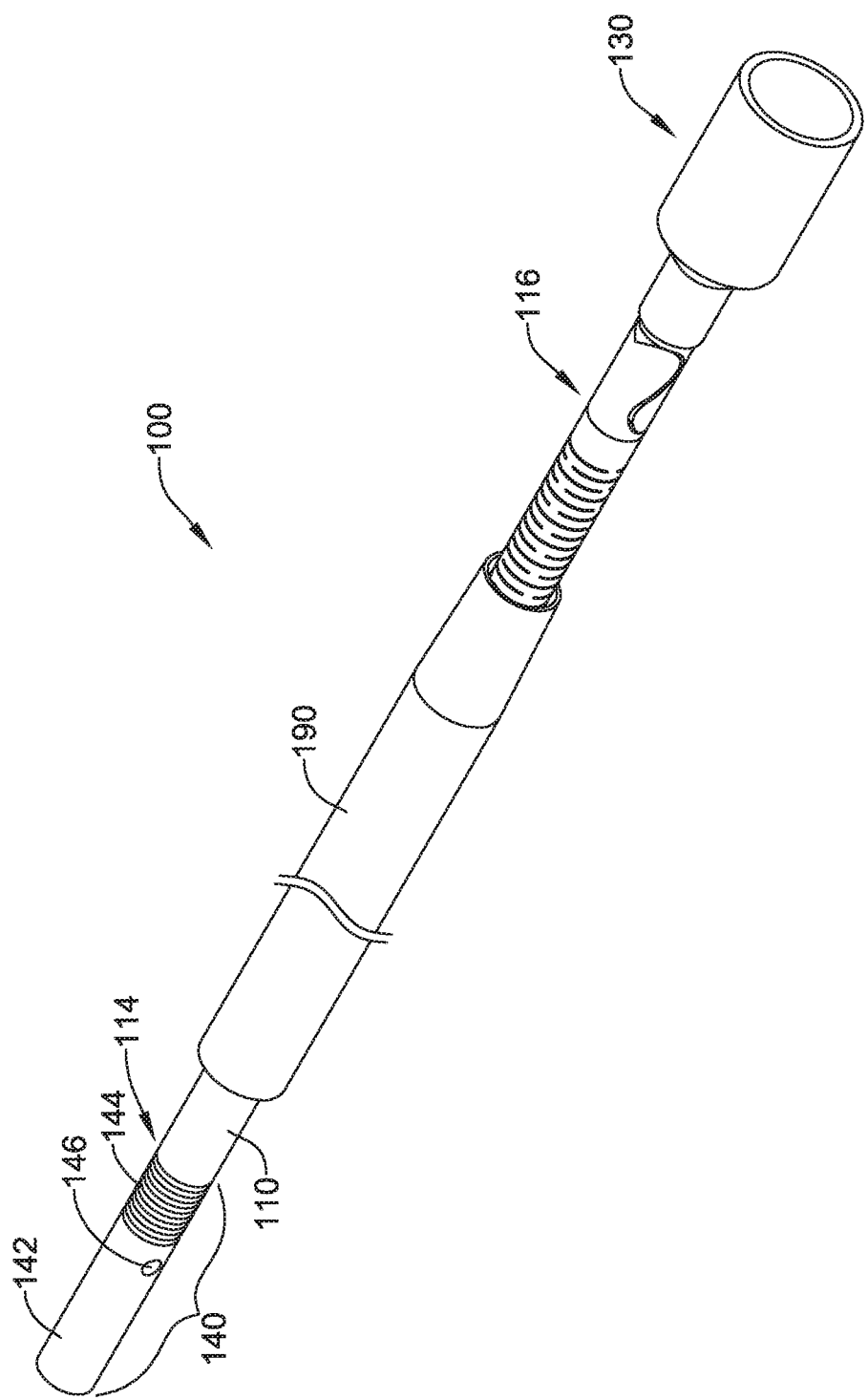
FIG. 1 is a perspective view of an example medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless specifically referred to as a minimum extent. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage. However, where referred to as a "minimum extent", the "extent" shall refer to a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact and/or are affected by the cardiovascular system are prevalent throughout the world. For example, some forms of arterial venous malformations (AVMs) may "feed" off of normal blood flow through the vascular system. Without being bound by theory, it is believed that it may be possible to treat, at least partially, arterial venous malformations and/or other diseases or conditions by starving them of normal, oxygen and/or nutrient-rich blood flow, thereby limiting their ability to grow and/or spread. Other examples of diseases or conditions that may benefit from vascular occlusion include, but are not limited to, bleeds, aneurysms, venous insufficiency, shutting off blood flow prior to organ resection, or preventing embolic bead reflux into branch vessels in the liver. Disclosed herein are medical devices that may be used within a portion of the cardiovascular system in order to treat and/or repair some arterial venous malformations and/or other diseases or conditions. The devices disclosed herein may also provide a number of additional desirable features and benefits as described in more detail below.

Figure 2:
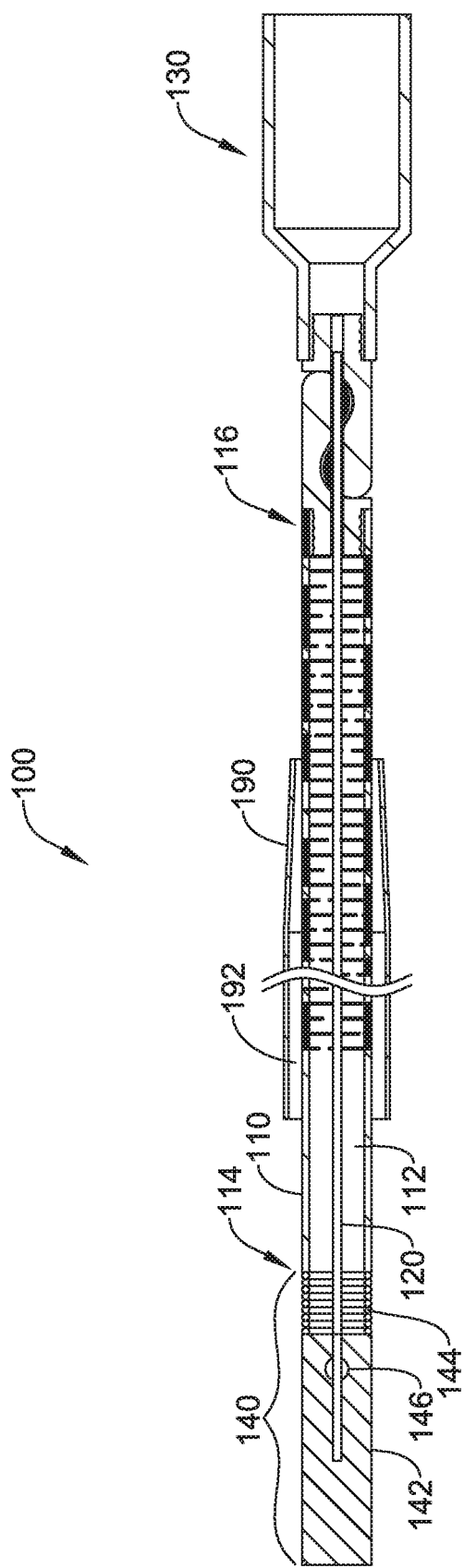
FIG. 2 is a partial cut-away view of an example medical device system.

FIGS. 1 and 2 illustrate aspects of an example medical device system 100. The medical device system 100 may include an elongate shaft 110 having a lumen 112 (e.g., FIG. 2) extending from a proximal end 114 of the elongate shaft 110 to a distal end 116 of the elongate shaft 110. In some embodiments, the elongate shaft 110 may be a catheter, a hypotube, or other similar tubular structure. In some embodiments, at least a portion of the elongate shaft 110 may include micromachining, a plurality of cuts or weakened areas, some degree of material removal, etc. to provide increased flexibility along a length of the elongate shaft 110 for navigating tortuous vasculature. Some suitable but non-limiting materials for the elongate shaft 110, for example metallic materials, polymer materials, composite materials, etc., are described below.

The medical device system 100 may include a release wire 120 (e.g., FIG. 2) slidably disposed within the lumen 112 of the elongate shaft 110. A medical device 130 may be disposed proximate the distal end 116 of the elongate shaft 110. The release wire 120 may be axially slidable between an interlocked position and a released position. The release wire 120 may be configured to releasably attach the medical device 130 to the distal end 116 of the elongate shaft 110. The medical device 130 may be configured to expand from a delivery configuration to a deployed configuration. For simplicity, the medical device 130 is illustrated herein as a vascular occlusion device, but other suitable medical devices transported, delivered, used, released, etc. in a similar manner are also contemplated, including but not limited to, embolic coils, stents, embolic filters, replacement heart valves, other occlusion devices, and/or other medical implants, etc. In some embodiments, the release wire 120 may be alternately and/or interchangeably referred to as a pull wire, an actuation wire, and/or a locking wire. The release wire 120 may generally be a solid wire or shaft, but may also be tubular in some embodiments. Some suitable but non-limiting materials for the release wire 120, for example metallic materials, polymer materials, composite materials, etc., are described below.

Figure 8:
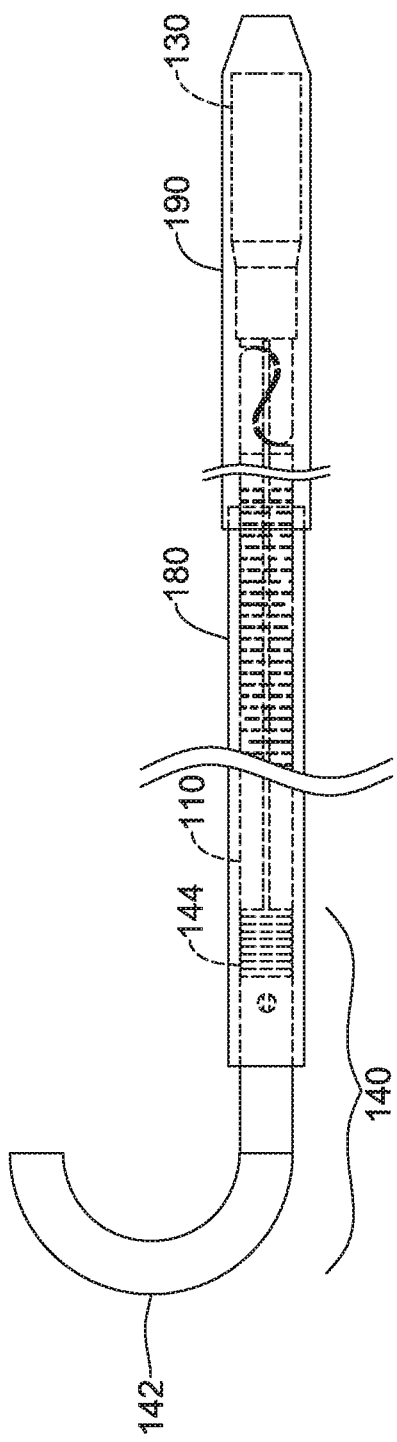
FIGS. 8-9 illustrate an example securement member during loading of an example medical device system.

In some embodiments, the medical device system 100 may include a microcatheter 190 sized and configured to deliver the medical device 130 to a treatment site in a delivery configuration. The elongate shaft 110 and the medical device 130 may be slidably disposed within a lumen 192 (e.g., FIG. 2) of the microcatheter 190. In some embodiments, the microcatheter 190 may facilitate percutaneous delivery of the medical device 130 to the treatment site. For reference only, the medical device 130 may be shown in the figures (e.g., FIGS. 1-2 and 5-7) in the deployed configuration or an at least partially-deployed configuration. The skilled person will recognize that the medical device 130 may be radially constrained into the delivery configuration when the medical device 130 is disposed within the lumen 192 of the microcatheter 190 (e.g., FIGS. 8-9). Some suitable but non-limiting materials for the microcatheter 190, for example metallic materials, polymer materials, composite materials, etc., are described below.

As seen in FIGS. 1 and 2, the medical device system 100 may include a securement member 140 fixedly attached to and/or extending proximally from the proximal end 114 of the elongate shaft 110, and fixedly attached to a proximal end of the release wire 120. The securement member 140 may include a proximal portion 142, a distal portion 144, and an attachment aperture 146 extending laterally and/or radially into the proximal portion 142 of the securement member 140 from an outer surface of the proximal portion 142 of the securement member 140.

In some embodiments, the proximal portion 142 of the securement member 140 may be fixedly attached to the distal portion 144 of the securement member 140. In some embodiments, the proximal portion 142 of the securement member 140 may be integrally formed with the distal portion 144 of the securement member 140 as a single unitary structure. The proximal portion 142 of the securement member 140 may take one or more of several different forms, including but not limited to, a generally solid member, a tubular member, or combinations thereof. For example, the proximal portion 142 of the securement member 140 may include an axial lumen extending along a central longitudinal axis of the medical device system 100, the elongate shaft 110, the release wire 120, and/or the securement member 140, the axial lumen being configured to receive a proximal end of the release wire 120. In some embodiments, the attachment aperture 146 extending laterally and/or radially into the proximal portion 142 of the securement member 140 from an outer surface of the proximal portion 142 of the securement member 140 may intersect with the axial lumen extending along the central longitudinal axis of the medical device system 100, the elongate shaft 110, the release wire 120, and/or the securement member 140. The attachment aperture 146 extending laterally and/or radially into the proximal portion 142 of the securement member 140 from an outer surface of the proximal portion 142 of the securement member 140 may be used to fixedly attached the proximal end of the release wire 120 to the proximal portion 142 of the securement member 140, for example, using an adhesive, a bonding agent, a weld, or other means of attachment.

Figure 3:
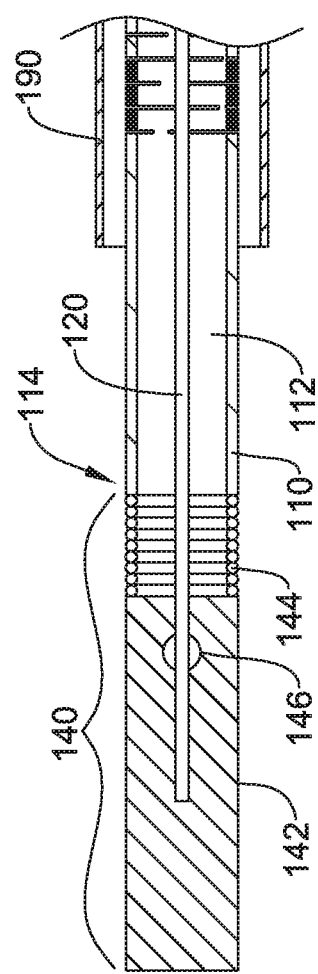
FIG. 3 is partial cut-away view of a portion of an example medical device system.
Figure 4:
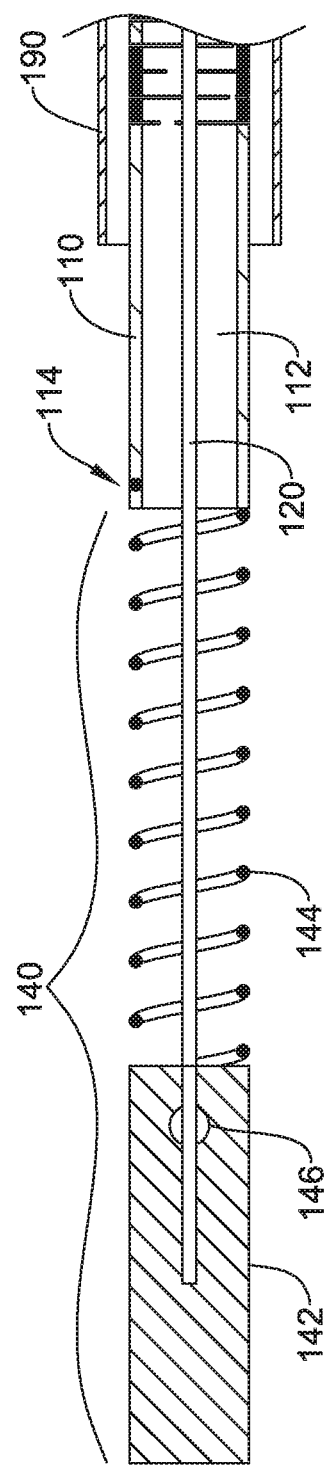
FIG. 4 is partial cut-away view of a portion of an example medical device system.

In some embodiments, the proximal portion 142 of the securement member 140 may be configured to translate proximally away from the proximal end 114 of the elongate shaft 110 upon application of a proximally-directed force to the proximal portion 142 of the securement member 140 while the elongate shaft 110 is maintained in a fixed position, as seen in FIGS. 3 and 4. Additionally, in some embodiments, the proximal portion 142 of the securement member 140 remains connected to the proximal end 114 of the elongate shaft 110, for example by the distal portion 144 of the securement member 140, after proximal translation of the proximal portion 142 of the securement member 140 away from the proximal end of the elongate shaft 110.

The distal portion 144 of the securement member 140 may be fixedly attached to the proximal end 114 of the elongate shaft 110. In some embodiments, the distal portion 144 of the securement member 140 may be a coil spring or a helical member. In at least some embodiments, an outer surface of the distal portion 144 of the securement member 140 may be fixedly attached to an inner surface of the elongate shaft 110 (e.g., a surface defining the lumen 112). In some embodiments, an inner surface of the distal portion 144 of the securement member 140 may be fixedly attached to an outer surface of the elongate shaft 110. In some embodiments, a distal end of the distal portion 144 of the securement member 140 may be embedded in the proximal end 114 of the elongate shaft 110. In some embodiments, the distal portion 144 may be integrally formed with and/or from the elongate shaft 110. For example, in some embodiments, the distal portion 144 may be cut from a portion of the securement member 140 and/or the elongate shaft 110 (as a helical member or coil spring, for example).

In some embodiments, the proximal portion 142 of the securement member 140 may be visually distinguishable from the distal portion 144 of the securement member 140 and/or the proximal end 114 of the elongate shaft 110. For example, the proximal portion 142 of the securement member 140 may have and/or include a different coloration from the distal portion 144 of the securement member 140 and/or the elongate shaft 110, a different exterior marking scheme from the distal portion 144 of the securement member 140 and/or the elongate shaft 110, a different exterior texture or surface treatment from the distal portion 144 of the securement member 140 and/or the elongate shaft 110, and/or other and/or additional means of visually distinguishing the proximal portion 142 of the securement member 140 from the distal portion 144 of the securement member 140 and/or the proximal end 114 of the elongate shaft 110. Some suitable but non-limiting materials for the securement member 140, the proximal portion 142, and/or the distal portion 144, for example metallic materials, polymer materials, composite materials, etc., are described below.

A wall of the distal portion 144 of the securement member 140 (and/or the coil spring or helical member) may define a lumen, as seen in FIGS. 3 and 4 for example, wherein the release wire 120 is slidably disposed within the lumen of the distal portion 144 of the securement member 140 (and/or the coil spring or helical member). The lumen of the distal portion 144 of the securement member 140 (and/or the coil spring or helical member) may be coaxial with and/or fluidly connected to the lumen 112 of the elongate shaft 110.

Proximal axial translation of the proximal portion 142 of the securement member 140 away from and/or relative to the proximal end 114 of the elongate shaft 110 may elongate the distal portion 144 of the securement member 140 (and/or the coil spring or helical member) and translate the release wire 120 relative to the elongate shaft 110 from the interlocked position to the released position to release the medical device 130 from the distal end 116 of the elongate shaft 110, as will be explained in more detail herein.

Figure 5:
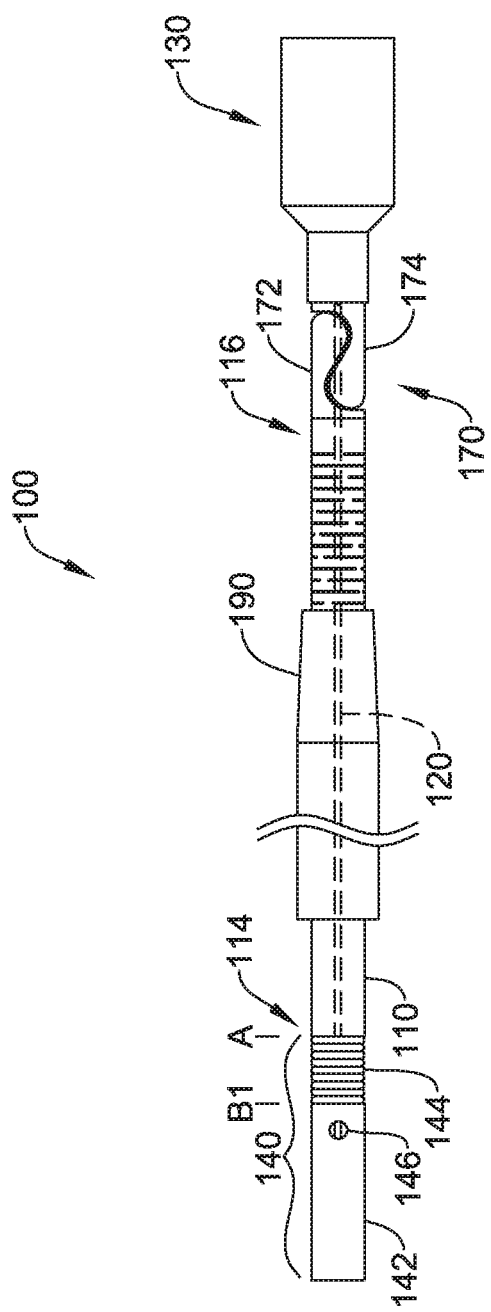
FIGS. 5-6 illustrate actuation of a portion of an example medical device system.
Figure 6:
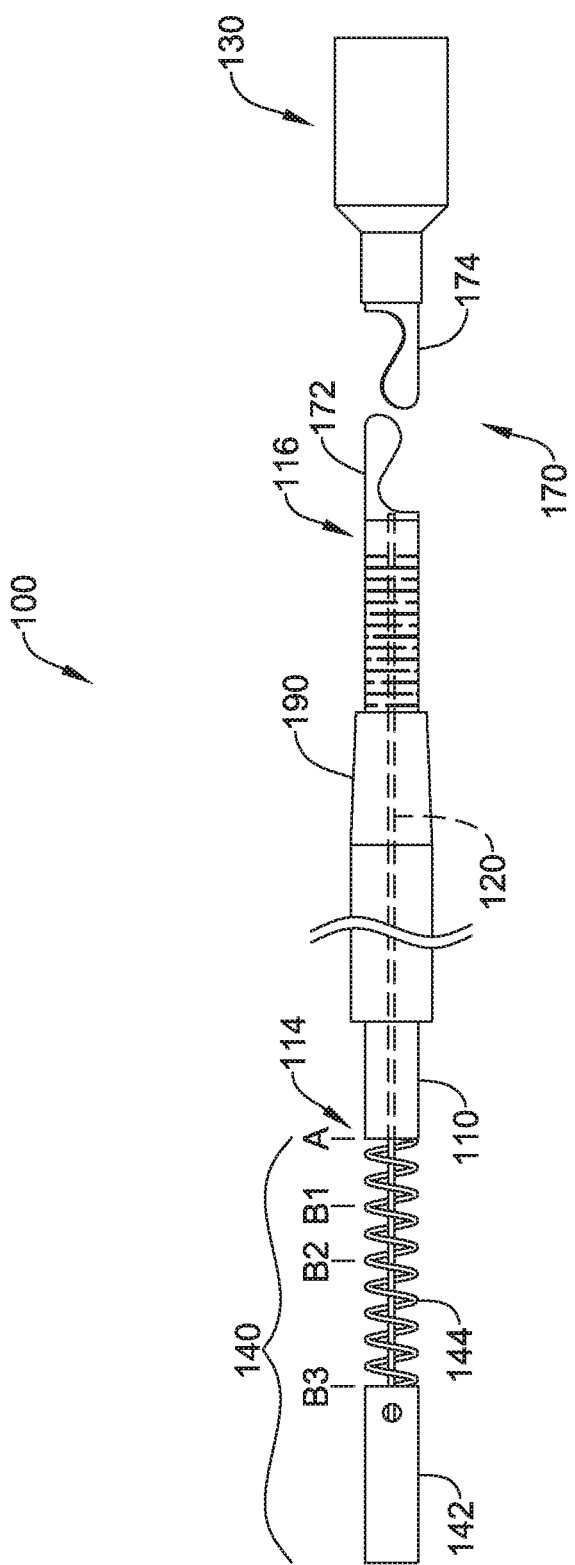
Figure 7:
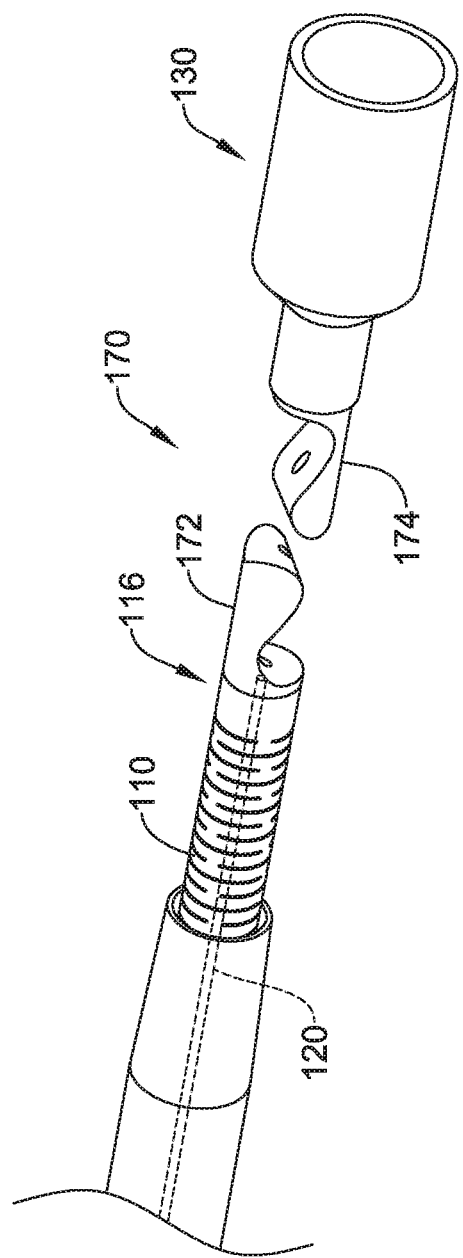
FIG. 7 illustrates an example release mechanism of an example medical device system.

FIGS. 5 and 6 generally illustrate the medical device 130 being released from the elongate shaft 110, such as at a treatment site, for example. In use, the microcatheter 190 of the medical device system 100 may be inserted into a patient's anatomy and a distal end of the microcatheter 190 may be guided and/or advanced to a location adjacent a treatment site. The medical device 130 disposed at and/or proximate the distal end 116 of the elongate shaft 110 may be inserted into a proximal end of the lumen 192 (e.g., FIG. 2) disposed within the microcatheter 190 and advanced through and/or with the microcatheter 190 to the treatment site. In some embodiments, the medical device 130 may be disposed within the lumen 192 of the microcatheter 190 proximate the distal end of the microcatheter 190. In some embodiments, the medical device 130 may be disposed within the lumen 192 of the microcatheter 190 proximate the distal end of the microcatheter 190 prior to use and/or prior to inserting the microcatheter 190 into the patient's anatomy (see, e.g., FIG. 8). Deployment and/or release of the medical device 130 may be performed selectively depending upon the type of medical device and/or the desired treatment process or method. When ready to deploy the medical device 130, the elongate shaft 110 may be advanced and/or translated distally relative to the microcatheter 190 until the medical device 130 is exposed and/or disposed distal of the microcatheter 190, as seen in FIG. 5. Alternatively, the microcatheter 190 may be withdrawn relative to the elongate shaft 110 until the medical device 130 is exposed and/or disposed distal of the microcatheter 190.

A release mechanism 170 may releasably attach the medical device 130 to the distal end 116 of the elongate shaft 110. In some embodiments, the elongate shaft 110 may include a first portion 172 of the release mechanism 170 fixedly attached to the distal end 116 of the elongate shaft 110 and the medical device 130 may include a second portion 174 of the release mechanism 170 fixedly attached to a proximal end of the medical device 130. A distal end of the release wire 120 may slidably engage with the first portion 172 of the release mechanism 170 and the second portion 174 of the release mechanism 170 in the interlocked position, as seen in FIG. 5. The release wire 120 interlocks the first portion 172 of the release mechanism 170 with the second portion 174 of the release mechanism 170 when the proximal portion 142 of the securement member 140 is biased distally by the distal portion 144 of the securement member 140 (and/or the coil spring or helical member) toward and/or in the interlocked position. For example, when the proximal portion 142 of the securement member 140 is translated proximally away from the proximal end 114 of the elongate shaft 110 (e.g., from an initial axial location B1 away from and/or relative to a reference location A, corresponding to the proximal end 114 of the elongate shaft 110, toward a predetermined axial location B2 and/or a releasing axial location B3), as seen in FIG. 6, the release wire 120 is translated in a proximal direction relative to the elongate shaft 110 toward the released position to release the second portion 174 of the release mechanism 170 and/or the medical device 130 from the first portion 172 of the release mechanism 170 and/or the elongate shaft 110, as seen in more detail in FIG. 7. In at least some embodiments, the release wire 120 may be slidably disposed within the distal portion 144 of the securement member 140 (and/or the coil spring or helical member), the lumen 112 extending through the elongate shaft 110, a first axial lumen extending through the first portion 172 of the release mechanism 170, and a second axial lumen extending through the second portion 174 of the release mechanism 170. The first axial lumen of the first portion 172 and the second axial lumen of the second portion 174 may be substantially coaxial with the central longitudinal axis and/or the release wire 120 when the medical device 130 is releasably attached to the distal end 116 of the elongate shaft 110. Some suitable but non-limiting materials for the release mechanism 170, the first portion 172, and the second portion 174, for example metallic materials, polymer materials, composite materials, etc., are described below.

Referring back to FIGS. 5 and 6, the elongate shaft 110 may have sufficient length that the proximal end 114 of the elongate shaft 110 and/or the securement member 140 remains proximal of (e.g., extends proximally from) the microcatheter 190 when the medical device 130 is disposed distal of the microcatheter 190. In use, the elongate shaft 110 may have sufficient length to reach from the treatment site to a position outside of the patient where the medical device system 100 may be manipulated by an operator (e.g., clinician, physician, user, etc.). After insertion of the medical device system 100 to the treatment site, the operator of the medical device system 100 may place a first hand on the proximal end 114 of the elongate shaft 110 and a second hand on the proximal portion 142 of the securement member 140 in order to manipulate the proximal portion 142 of the securement member 140 and/or the release wire 120 to release the medical device 130. The distal portion 144 of the securement member 140 (and/or the coil spring or helical member) may be disposed proximal of a proximal end of the microcatheter 190 when the medical device 130 is disposed distal of the microcatheter 190.

In at least some embodiments, the securement member 140 may resist axial translation of the release wire 120 relative to the elongate shaft 110 and/or the medical device 130 (e.g., from the interlocked position to the released position). The distal portion 144 of the securement member 140 (and/or the coil spring or helical member) may be configured to bias the proximal portion 142 of the securement member 140 distally toward the proximal end 114 of the elongate shaft 110 and/or an initial axial location B1 as discussed further herein (see, e.g., FIGS. 5-6). For example, the distal portion 144 of the securement member 140 (and/or the coil spring or helical member) may be configured to be in tension between the proximal portion 142 of the securement member 140 and the proximal end 114 of the elongate shaft 110, thereby pulling the proximal portion 142 of the securement member 140 and the proximal end 114 of the elongate shaft 110 towards each other and resisting axial translation of the proximal portion 142 of the securement member 140 proximally away from the proximal end 114 of the elongate shaft 110. When the proximal portion 142 of the securement member 140 is disposed at the initial axial location B1, the release wire 120 may be considered to be in the interlocked position.

In at least some embodiments, the distal portion 144 of the securement member 140 (and/or the coil spring or helical member) may undergo elastic deformation during proximal translation of the proximal portion 142 of the securement member 140 relative to the elongate shaft 110 up to a predetermined axial location B2, as discussed herein (e.g., FIGS. 5-6). Upon releasing the proximal portion 142 of the securement member 140 after proximal translation of the proximal portion 142 of the securement member 140 relative to the elongate shaft 110 up to the predetermined axial location B2, the distal portion 144 of the securement member 140 (and/or the coil spring or helical member) may translate the proximal portion 142 of the securement member 140 distally toward the proximal end 114 of the elongate shaft 110 and/or the initial axial location B1. As such, at substantially any axial location of the proximal portion 142 of the securement member 140 between the initial axial location B1 and the predetermined axial location B2, the release wire 120 interlocks the first portion 172 of the release mechanism 170 with the second portion 174 of the release mechanism 170 and thus may be considered to be in the interlocked position, and the medical device 130 remains attached to the elongate shaft 110. Additionally, at substantially any axial location of the proximal portion 142 of the securement member 140 between the initial axial location B1 and the predetermined axial location B2, the distal portion 144 of the securement member 140 is configured to elastically urge and/or return the proximal portion 142 of the securement member 140 towards the initial axial location B1. At the axial locations between the initial axial location B1 and the predetermined axial location B2, release of the medical device 130 may be considered fully reversible and the release wire 120 may be distally advanceable back through the first portion 172 of the release mechanism 170 and the second portion 174 of the release mechanism 170 to fully re-engage the medical device 130 to the elongate shaft 110, to reposition the medical device 130 for example.

In at least some embodiments, the distal portion 144 of the securement member 140 (and/or the coil spring or helical member) may undergo plastic deformation after proximal translation of the proximal portion 142 of the securement member 140 relative to the elongate shaft 110 past the predetermined axial location B2 up to a releasing axial location B3, as discussed herein (e.g., FIGS. 5-6). In some embodiments, the releasing axial location B3 may correspond to a maximum or upper limit of stretch and/or elongation of the distal portion 144 of the securement member 140 (and/or the coil spring or helical member). In some embodiments, the distal portion 144 of the securement member 140 (and/or the coil spring or helical member) may be capable of stretching and/or elongating past the releasing axial location B3. Upon releasing the proximal portion 142 of the securement member 140 after proximal translation of the proximal portion 142 of the securement member 140 relative to the elongate shaft 110 past the predetermined axial location B2, an axial position of the proximal portion 142 of the securement member 140 remains substantially fixed relative to the proximal end 114 of the elongate shaft 110 and/or the initial axial location B1.

At any axial location between the predetermined axial location B2 and the releasing axial position B3, plastic deformation of the distal portion 144 of the securement member 140 has occurred and release of the medical device 130 may be considered to be irreversible in that full re-engagement of the release wire 120 with the first portion 172 of the release mechanism 170 and the second portion 174 of the release mechanism 170 is no longer possible. However, at any axial location between the predetermined axial location B2 and the releasing axial position B3, the release wire 120 is still partially engaged with and/or extending at least partially through the first portion 172 of the release mechanism 170 and the second portion 174 of the release mechanism 170, and the medical device 130 is still attached to the elongate shaft 110 and may be removed from the patient's anatomy by withdrawing the medical device 130 proximally into the lumen 192 of the microcatheter 190. As such, full release is not strictly required, but the ability to reposition the medical device 130 may be limited or terminated at any axial location between the predetermined axial location B2 and the releasing axial position B3.

In some embodiments, the release wire 120 may include at least one indicator configured to visually communicate a deformation status of the distal portion 144 of the securement member 140 (and/or the coil spring or helical member). For example, the at least one indicator may be configured to visually communicate to a user whether the distal portion 144 of the securement member 140 (and/or the coil spring or helical member) is undergoing elastic deformation or plastic deformation, and/or whether the distal portion 144 of the securement member 140 (and/or the coil spring or helical member) is within an elastic deformation region or a plastic deformation region. In some embodiments, the at least one indicator may include at least one colored portion of the release wire 120, wherein each colored portion corresponds to one and/or a different deformation status.

For example, in some embodiments, the at least one indicator may include a first indicator configured to visually communicate to the user that the distal portion 144 of the securement member 140 (and/or the coil spring or helical member) is undergoing elastic deformation and/or is within an elastic deformation region (e.g., at the axial locations between the initial axial location B1 and the predetermined axial location B2). In some embodiments, the at least one indicator may include a second indicator configured to visually communicate to the user that the distal portion 144 of the securement member 140 (and/or the coil spring or helical member) is undergoing plastic deformation and/or is within a plastic deformation region (e.g., at any axial location past the predetermined axial location B2, and/or at any axial location between the predetermined axial location B2 and the releasing axial position B3). In some embodiments, the first indicator may be a first colored region of the release wire 120 visible through and/or within the distal portion 144 of the securement member 140 (and/or the coil spring or helical member). In some embodiments, the second indicator may be a second colored region of the release wire 120 visible through and/or within the distal portion 144 of the securement member 140 (and/or the coil spring or helical member), wherein the second colored region of the release wire 120 is a different color than the first colored region of the release wire 120.

In some embodiments, the at least one indicator, the first indicator, the first colored region, the second indicator, and/or the second colored region may be formed and/or presented as a reflowed polymer on the release wire 120 or a colored metallic material secured (e.g., crimped, welded, adhered/glued, etc.) to the release wire 120. Other means of forming and/or presenting the at least one indicator, the first indicator, the first colored region, the second indicator, and/or the second colored region, including but not limited to anodizing, plating, laser marking, chemical modification, etc., are also contemplated.

At any axial location of the proximal portion 142 of the securement member 140 proximally past the releasing axial location B3, the release wire 120 releases the first portion 172 of the release mechanism 170 from the second portion 174 of the release mechanism 170 and thus may be considered to be in the released position, and the medical device 130 is released from the elongate shaft 110. Further proximal axial translation of the proximal portion 142 of the securement member 140 relative to the elongate shaft 110 past the releasing axial location B3 may provide additional clearance and/or require less precision from the practitioner while safely releasing the medical device 130.

In some embodiments, the proximal portion 142 of the securement member 140 may assume a generally linear configuration when unconstrained, as seen in FIGS. 1-6. Alternatively, in some embodiments, the proximal portion 142 of the securement member 140 may assume a non-linear configuration (e.g., curved, bent, zig-zag, undulating, sinuous, etc.) when unconstrained, one example of which may be seen in FIG. 8. The medical device system 100 may include an introducer 180 configured to load the medical device 130 into the microcatheter 190. The introducer 180 may be a tubular member having a lumen extending from a proximal end to a distal end. While illustrated in conjunction with the non-linear configuration of the proximal portion 142 of the securement member 140 in FIGS. 8-9, the skilled person will recognize that the introducer 180 may be useful in all configurations of the proximal portion 142 of the securement member 140, including the linear configuration shown in FIGS. 1-6. The introducer 180 may hold the medical device 130 to a reduced diameter and/or in a delivery configuration for loading into the microcatheter 190. After loading the medical device 130 into the microcatheter 190, the introducer 180 may be proximally withdrawn over and relative to the elongate shaft 110 and the securement member 140 and removed from the medical device system 100.

Figure 9:
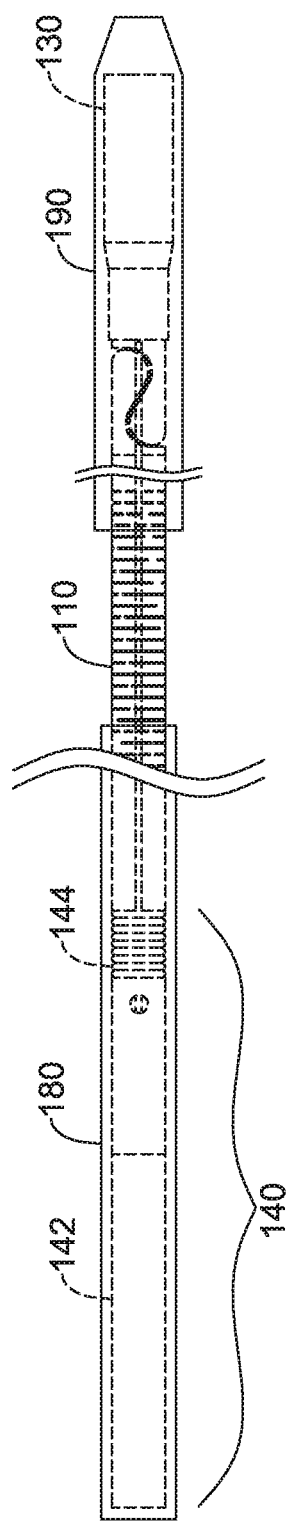

In at least some embodiments having the proximal portion 142 of the securement member 140 which assumes the non-linear configuration when unconstrained, proximal withdrawal of the introducer 180 over and relative to the securement member 140, and in particular over and relative to the proximal portion 142 of the securement member 140, may urge, constrain, and/or position the proximal portion 142 of the securement member 140 into a substantially linear configuration while the proximal portion 142 of the securement member 140 is disposed within the lumen of the introducer 180, as seen in FIG. 9. Further proximal withdrawal and/or removal of the introducer 180 from the proximal portion 142 of the securement member 140 may remove the constraint created by the introducer 180 and thereafter permit the proximal portion 142 of the securement member 140 to return to and/or assume the non-linear configuration. The non-linear configuration of the proximal portion 142 of the securement member 140 may be convenient and/or beneficial for identification, grasping, and/or manipulation of the proximal portion 142 of the securement member 140 by the practitioner.

In an alternative configuration, the introducer 180 may be configured to assume the non-linear configuration of the proximal portion 142 of the securement member 140 when the introducer 180 is withdrawn proximally over and/or relative to the proximal portion 142 of the securement member 140. For example, the introducer 180 may be made from a flexible material that permit the introducer 180 to flex, deflect, and/or bend to conform to the non-linear configuration of the proximal portion 142 of the securement member 140 as the introducer 180 is translated over the proximal portion 142 of the securement member 140. Other configurations are also contemplated.

In use, a method of delivering the medical device 130 to a treatment site (e.g., a vein, an artery, etc.) may include inserting the microcatheter 190 into a patient's anatomy and guiding the distal end of the microcatheter 190 to a location adjacent the treatment site. The method may include inserting the medical device 130 disposed at and/or proximate the distal end 116 of the elongate shaft 110 into a proximal end of the lumen 192 disposed within the microcatheter 190. In some embodiments, the medical device 130 may be inserted into the lumen 192 of the microcatheter 190 after the microcatheter 190 is inserted into the patient's anatomy. The method may include advancing the medical device 130 through the microcatheter 190 to the treatment site. The medical device 130 may be releasably attached to the distal end 116 of the elongate shaft 110 by a pull wire (e.g., the release wire 120, etc.) extending through the lumen 112 within the elongate shaft 110. The securement member 140 may extend proximally from the elongate shaft 110, and the securement member 140 may be fixedly attached to the elongate shaft 110 and the pull wire (e.g., the release wire 120, etc.), as described herein. Alternatively, in some embodiments, the medical device 130 may be inserted into the proximal end of the lumen 192 of the microcatheter 190 and advanced through the microcatheter 190 to a distal end of the microcatheter 190 before the microcatheter 190 is inserted into the patient's anatomy.

As discussed herein, the proximal portion 142 of the securement member 140 may be fixedly attached to a proximal end of the pull wire (e.g., the release wire 120, etc.) and the distal portion 144 of the securement member 140 may be fixedly attached to the proximal end 114 of the elongate shaft 110. The first portion 172 of the release mechanism 170 may be attached to the distal end 116 of the elongate shaft 110, and the second portion 174 of the release mechanism 170 may be fixedly attached to a proximal end of the medical device 130. The pull wire (e.g., the release wire 120, etc.) may be slidably disposed within a lumen of the distal portion 144 of the securement member 140, the lumen 112 of the elongate shaft 110, the first axial lumen of the first portion 172 of the release mechanism 170, and the second axial lumen of the second portion 174 of the release mechanism 170.

The method may include translating the proximal portion 142 of the securement member 140 proximally away from the proximal end 114 of the elongate shaft 110 while the elongate shaft 110 is maintained in a fixed position with respect to the treatment site to translate the pull wire (e.g., the release wire 120, etc.) relative to the elongate shaft 110 and/or the release mechanism 170 to shift the pull wire (e.g., the release wire 120, etc.) from an interlocked position to a released position, thereby releasing the medical device 130 from the elongate shaft 110. As discussed herein, the proximal portion 142 of the securement member 140 remains connected to the proximal end 114 of the elongate shaft 110 after proximal translation away from the proximal end 114 of the elongate shaft 110, by the distal portion 144 of the securement member 140 for example.

The method may also include proximal withdrawal of the elongate shaft 110 and/or the microcatheter 190 from the treatment site. For example, in some embodiments, the elongate shaft 110 may be withdrawn proximally through the lumen 192 of the microcatheter 190 and removed, and the microcatheter 190 may then be withdrawn and/or removed from the patient's anatomy. In some embodiments, the elongate shaft 110 may be withdrawn proximally far enough for the distal end 116 of the elongate shaft 110 and/or the first portion 172 of the release mechanism 170 to be positioned within the distal end and/or the lumen 192 of the microcatheter 190. The elongate shaft 110 and the microcatheter 190 may then be withdrawn together from the patient's anatomy.

In some embodiments, the elongate shaft 110 may be removed through the lumen 192 of the microcatheter 190, and the microcatheter 190 may be left and/or held in place within the patient's anatomy. If needed, a second elongate shaft and associated second medical device may then be inserted into the proximal end of the lumen 192 of the microcatheter 190 and advanced to the treatment site for deployment. Additional repetitions of the device(s) described herein, as well as the described method steps, may be used as needed or desired for a particular procedure.

The materials that can be used for the various components of the medical device system 100, the elongate shaft 110, the release wire 120, the medical device 130, the securement member 140, the release mechanism 170, the introducer 180, and/or the microcatheter 190, etc. (and/or other systems disclosed herein) and the various elements thereof disclosed herein may include those commonly associated with medical devices. For simplicity purposes, the following discussion makes reference to the medical device system 100, the elongate shaft 110, the release wire 120, the medical device 130, the securement member 140, the release mechanism 170, the introducer 180, and/or the microcatheter 190, etc. However, this is not intended to limit the devices and methods described herein, as the discussion may be applied to other elements, members, components, or devices disclosed herein, such as, but not limited to, the medical device system 100, the elongate shaft 110, the release wire 120, the medical device 130, the securement member 140, the release mechanism 170, the introducer 180, and/or the microcatheter 190, etc. and/or elements or components thereof.

In some embodiments, the medical device system 100, the elongate shaft 110, the release wire 120, the medical device 130, the securement member 140, the release mechanism 170, the introducer 180, and/or the microcatheter 190, etc., and/or components thereof (such as, but not limited to, the proximal portion 142, the distal portion 144, the first portion 172, the second portion 174, etc.), may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the medical device system 100, the elongate shaft 110, the release wire 120, the medical device 130, the securement member 140, the release mechanism 170, the introducer 180, and/or the microcatheter 190, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the medical device system 100, the elongate shaft 110, the release wire 120, the medical device 130, the securement member 140, the release mechanism 170, the introducer 180, and/or the microcatheter 190, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 100, the elongate shaft 110, the release wire 120, the medical device 130, the securement member 140, the release mechanism 170, the introducer 180, and/or the microcatheter 190, etc. to achieve the same result.

In some embodiments, a degree of Magnetic Resonance Imaging (MM) compatibility is imparted into the medical device system 100, the elongate shaft 110, the release wire 120, the medical device 130, the securement member 140, the release mechanism 170, the introducer 180, and/or the microcatheter 190, etc. For example, the medical device system 100, the elongate shaft 110, the release wire 120, the medical device 130, the securement member 140, the release mechanism 170, the introducer 180, and/or the microcatheter 190, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The medical device system 100, the elongate shaft 110, the release wire 120, the medical device 130, the securement member 140, the release mechanism 170, the introducer 180, and/or the microcatheter 190, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N®️ and the like), nitinol, and the like, and others.

In some embodiments, the medical device system 100, the elongate shaft 110, the release wire 120, the medical device 130, the securement member 140, the release mechanism 170, the introducer 180, and/or the microcatheter 190, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the medical device system 100, the elongate shaft 110, the release wire 120, the medical device 130, the securement member 140, the release mechanism 170, the introducer 180, and/or the microcatheter 190, etc. disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the medical device system 100, the elongate shaft 110, the release wire 120, the medical device 130, the securement member 140, the release mechanism 170, the introducer 180, and/or the microcatheter 190, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the medical device system 100, the elongate shaft 110, the release wire 120, the medical device 130, the securement member 140, the release mechanism 170, the introducer 180, and/or the microcatheter 190, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical device system, comprising:
   an elongate shaft having a lumen extending from a proximal end of the elongate shaft to a distal end of the elongate shaft;
   a release wire disposed within the lumen of the elongate shaft, wherein the release wire is configured to releasably attach a medical device to the distal end of the elongate shaft; and
   a securement member fixedly attached to the proximal end of the elongate shaft and to a proximal end of the release wire;
   wherein a proximal portion of the securement member is configured to translate proximally away from the proximal end of the elongate shaft upon application of a proximally-directed force to the proximal portion of the securement member while the elongate shaft is maintained in a fixed position;
   wherein the proximal portion remains connected to the proximal end of the elongate shaft after proximal translation away from the proximal end of the elongate shaft.

2. The medical device system of claim 1, wherein the proximal portion of the securement member is fixedly attached to the proximal end of the release wire and a distal portion of the securement member is fixedly attached to the proximal end of the elongate shaft.

3. The medical device system of claim 2, wherein the distal portion of the securement member is a coil spring.

4. The medical device system of claim 3, wherein the coil spring is configured to bias the proximal portion of the securement member distally toward the proximal end of the elongate shaft.

5. The medical device system of claim 4, wherein the coil spring undergoes elastic deformation during proximal translation of the proximal portion of the securement member up to a predetermined axial location.

6. The medical device system of claim 5, wherein upon releasing the proximal portion of the securement member after proximal translation of the proximal portion of the securement member up to the predetermined axial location, the coil spring translates the proximal portion of the securement member distally toward the proximal end of the elongate shaft.

7. The medical device system of claim 5, wherein the coil spring undergoes plastic deformation after proximal translation of the proximal portion of the securement member axially past the predetermined axial location.

8. The medical device system of claim 7, wherein upon releasing the proximal portion of the securement member after proximal translation of the proximal portion of the securement member axially past the predetermined axial location, an axial position of the proximal portion of the securement member remains substantially fixed relative to the proximal end of the elongate shaft.

9. The medical device system of claim 1, wherein proximal translation of the proximal portion of the securement member away from the proximal end of the elongate shaft translates the release wire axially relative to the elongate shaft.

10. The medical device system of claim 1, wherein the proximal portion of the securement member is visually distinguishable from the elongate shaft.

* * * * *